United States Patent [19]

Tsoglin et al.

[11] Patent Number: 5,469,859
[45] Date of Patent: Nov. 28, 1995

[54] NON-INVASIVE METHOD AND DEVICE FOR COLLECTING MEASUREMENTS REPRESENTING BODY ACTIVITY AND DETERMINING CARDIORESPIRATORY PARAMETERS OF THE HUMAN BODY BASED UPON THE MEASUREMENTS COLLECTED

[75] Inventors: Alexander Tsoglin, Beer Yakov; Yafim Frinerman, Bat-Yam, both of Israel

[73] Assignee: N.I. Medical Ltd., Tel-Aviv, Iceland

[21] Appl. No.: 82,606

[22] Filed: Jun. 24, 1993

[30] Foreign Application Priority Data

Jun. 24, 1992 [IL] Israel .......................... 102300

[51] Int. Cl.⁶ ................................................ A61B 5/085
[52] U.S. Cl. ................................................ 128/723
[58] Field of Search ................................. 128/671, 723, 128/734

[56] References Cited

U.S. PATENT DOCUMENTS

| | | | |
|---|---|---|---|
| 3,316,896 | 5/1967 | Thomasset | 128/734 |
| 3,347,223 | 10/1967 | Pacela | 128/734 |
| 4,506,678 | 3/1985 | Russell et al. | 128/723 |
| 4,562,843 | 1/1986 | Djordjevich et al. | 128/734 |
| 4,630,615 | 12/1986 | Yomtov | 128/734 |
| 4,781,201 | 11/1988 | Wright et al. | 128/723 |
| 4,794,934 | 1/1989 | Motoyama et al. | 128/734 |
| 4,805,621 | 2/1989 | Heinze et al. | 128/734 |
| 4,919,145 | 4/1990 | Marriott | 128/723 |
| 4,926,868 | 5/1990 | Larsen | 128/695 |
| 4,984,572 | 1/1991 | Cohen | 228/419 D |
| 5,109,863 | 5/1992 | Semmlow et al. | 128/715 |
| 5,178,154 | 1/1993 | Ackmann et al. | 128/713 |

OTHER PUBLICATIONS

Kushner et al., "Estimation of total body water by bioelectrical impedance analysis 1–3", Amer. Journal of Clinical Nutrition 44: Sep. 1986, pp. 417–418.
Huang et al., "Stroke volume measurements by electrical bioimpedance and echocardiography in healthy volunteers", Critical Care Medicine, vol. 18, no. 11, pp. 1274–1278, Nov. 1990.
Spinale et al., "Relationship of bioimpedance to thermodilution and echocardiographic measurements of cardiac function", Critical Care Medicine, vol. 18, No. 4, pp. 414–418, Apr. 1990.
Jewkes, et al., "Non–Invasive Measurement of Cardiac Output by Thoracic Electrical Bioimpedance: A Study of Reproducibility and Comparison with Thermodilution", British Journal of Anaesthesia 1991, 67, pp. 788–794.
Wang et al., "An Impedance Cardiography System: A New Design", Annals of Biomedical Engineering, vol. 17, pp. 535–556, 1989.
Renaissance Technologies, Inc., "IQ, What is the Working Principle Behind the IQ System", vol. 1.
Braden et al., "Noninvasive assessment of cardiac output in children using impedance cardiography", American Heart Journal, Nov. 1990, pp. 1166, 1171–1172.
Renaissance Technologies, Inc., "IQ: Noninvasive Hemodynamic Monitoring", 1992.
Miller et al., "Non Invasive Bioimpedance Measurement of Cardiac Output–A Validation Study", Annual Meeting of the Israel Heart Society, Apr. 1993.
"Introducing the Sorba Non–Invasive Cardiac Output Monitor", Sorba Medical Systems, Inc. 1990.

*Primary Examiner*—William E. Kamm
*Attorney, Agent, or Firm*—Helfgott & Karas

[57] ABSTRACT

A medical device, utilizing a non-invasive method for determining the main cardiorespiratory parameters of a patient's body, and employing a method of operation wherein two or four electrodes are applied to the patient's body in a manner enabling integral bioimpedance measurements of the total body of a patient to be effected. High stability amplitude alternating current is passed through the electrodes into the body so as to obtain an integral impedance curve of the body and derive therefrom simultaneous automatic separation of an active component. The desired cardiorespiratory parameters of the body are calculated from the active component of the integral bioimpedance, using empiric formulae applicable to integral bioimpedance measurements; the calculation being accomplished based on the average data obtained during a respiration cycle.

25 Claims, 7 Drawing Sheets

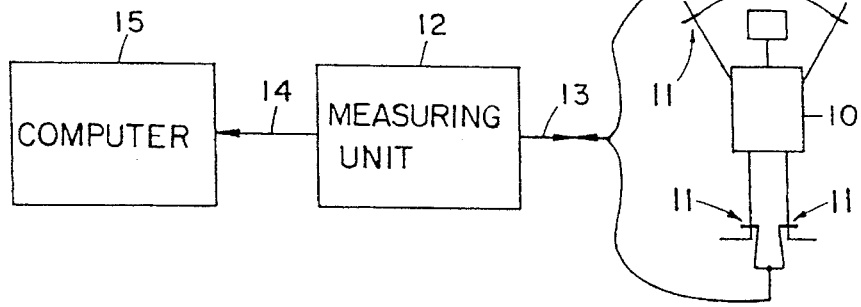
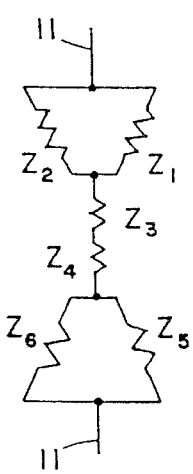
Fig.1A  Fig.1B
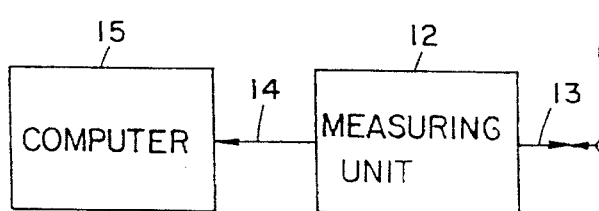
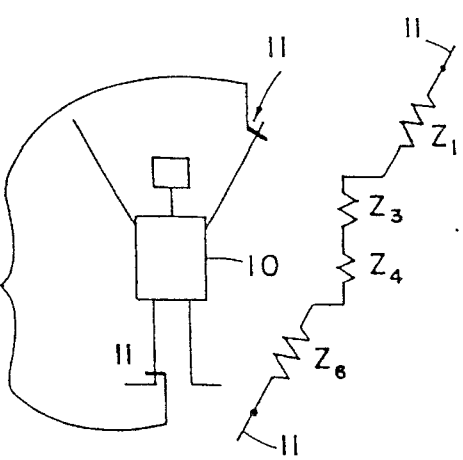
Fig.1C  Fig.1D
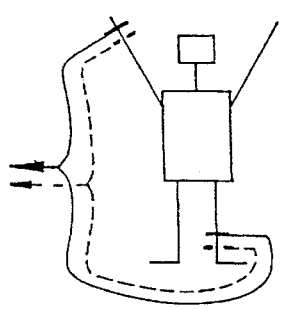
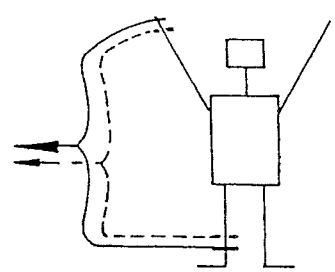
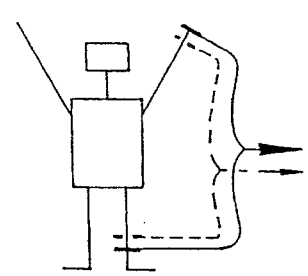
Fig.1E  Fig.1F  Fig.1G

NON-INVASIVE METHOD AND DEVICE FOR COLLECTING MEASUREMENTS REPRESENTING BODY ACTIVITY AND DETERMINING CARDIORESPIRATORY PARAMETERS OF THE HUMAN BODY BASED UPON THE MEASUREMENTS COLLECTED

FIELD OF THE INVENTION

The present invention relates to non-invasive cardiac and respiratory monitors, more particularly, to such systems for determining cardiac and respiratory performance using electrical bioimpedance measurements.

BACKGROUND OF THE INVENTION

Thermodilution is a well-known invasive procedure for enabling a physician to determine the main hemodynamic parameters of the human body. The patients investigated are admitted to the Intensive Care Unit and have pulmonary artery catheters inserted; the cardiac output direct measurements are made for clinical indications. Ice cold saline solution is used for the thermodilution measurements. This method is quite accurate, but it suffers from obvious disadvantages of an invasive diagnostic and treatment procedure.

Several non-invasive methods intended to substitute the invasive thermodilution procedure have been disclosed in the prior art. Two such modern non-invasive methods are widely known; the one method is based on echocardiographic measurements, and the second is the bioimpedance measurement method.

An obvious requirement of non-invasive techniques is the correlation of their results with the readings obtained by the basic invasive method, such as thermodilution. It has been found that the echocardiographic measurements are technically unsatisfactory in many cases.

On the other hand, the bioimpedance measurements, performed by modern impedance cardiographs, show reasonable correlation coefficients with thermodilution. (C. Jewkes and others: *British Journal of Anaesthesia* 1991; 67:788–794).

The validity of impedance cardiography is an important issue because of its potential usefulness in intensive care medicine. Impedance cardiography can be used in the intensive care unit to monitor changes in hemodynamic parameters (e.g. Cardiac Output, Systemic Vascular Resistance, etc.) as well as to gauge responses in these parameters to pharmacologic therapy. This technique would be most helpful for the postoperative cardiac patient, for clinical research of essential hypertension and for other cardiovascular diseases.

The bioelectric impedance of a living tissue or the whole body is the measurement of its opposition to an electric current passing therethrough between electrodes applied to the body. Different physiological activities producing variations in the value of the tissue's conductivity, cause changes in the distribution of the current density which are detected as variations in the impedance of these tissues or the whole body.

The impedance readings consist of the following three major components:
1. The base impedance ($Z_o$) arising from the electrical characteristics of the fundamental materials which make up the tissues (mainly, the extracell fluids).
2. The impedance change ($\delta Z$), synchronized with the cyclic cardiac activity. This component forms a line, called the rheogram, representing the information concerning the cardiac activity.
3. The impedance waveform ($\delta V$), accompanying the changes of the air volume and redistribution of the blood volume caused by respiration. The combination of these three components form a curve, which is called the plethysmogram by several researchers.

Consequently, three main groups of hemodynamic parameters are reflected in the plethysmogram and thus can be calculated therefrom.

Although electrical bioimpedance measurements have been studied for more than 30 years, it is only in recent years that clinical studies have documented the applicability of the bioimpedance measurements in the clinical setting.

Two main types of the Electrical Bioimpedance Measurements (EBM) are known in the prior art:

Local (segmentary) EBM of the variations in the blood volume, provided on specific parts of the body; the technique for thoracic EBM was suggested by Kubicek and colleagues in 1966, and then modified by Shramek and Bernstein; and Integral EBM of the whole body, enveloping practically the entire blood conducting system; the technique is described by M. Tishcenko (1968), Yakovlev (1973), Holzer (1970) and others. The integral EBM technique is a priori more informative than the segmentary EBM; however, no appropriate technical realization thereof has been recorded.

So far as the Segmentary-type of the Electrical Bioimpedance Measurements are concerned, it has been shown that Segmentary EBM employs a low level current applied to the thorax, where changes in the volume and velocity of blood flow in the thoracic aorta result in detectable changes in thoracic conductivity. Kubicek et al. demonstrated that the first derivative of the oscillating component of thoracic bioimpedance (dZ/dt) is linearly related to aortic blood flow. Using this relationship, empirical formulas were developed to estimate Stroke Volume (SV), and then Cardiac Output (CO). (Francis G. Spinale and others, *Critical Care Medicine*, 1990, Vol 18 No. 4, USA).

The original Minnesota Impedance Cardiograph was developed based on Kubicek's method. However, as reported by C. Jewkes and others, *British Journal of Anaesthesia* 1991; 67:788–794, this device produced different correlation coefficients with the thermodilution technique, varying from good (r=0.97) to poor (r=0.41).

Several achievements were then reported in the field defined by Kubicek and Shramek.

U.S. Pat. No. Re: 30,101 (William Kubicek et al.) describes an Impedance Plethysmograph. Cardiac output is measured by connecting excitation electrodes at the upper and lower ends of the thorax of a patient, and connecting measuring electrodes to the thorax between the excitation electrodes. A constant fluctuating excitation current is applied to the excitation electrodes, and any changes in impedance within the thorax are measured, whilst simultaneously measuring the beginning and the end of a systole. Cardiac output is determined by measuring the maximum decreasing impedance slope during the systole.

U.S. Pat. No. 4,450,527 (Bohumir Shramek), assigned to one of the leading companies in the field, BoMED® Medical Manufacturing Ltd., describes a non-invasive continuous cardiac output monitor. The system disclosed eliminates the effect of respiration from the thoracic impedance as a function of time, so as continuously to provide a signal of pulsatile thoracic impedance changes. The pulsatile thoracic impedance signal is processed to produce signals indicative of the ventricular ejection time and the maximum rate of change of the pulsatile thoracic impedance, which are fed to a microprocessor in order to calculate the volume of blood pumped per stroke according to an improved systolic upstroke equation.

BoMED® continued its activity in the described field and is now offering several products. One of them is the BoMED® NCCOM3 (Irvine, Calif.). It has replaced the band electrodes of the original Minnesota Impedance Cardiograph with pairs of standard ECG electrodes, which improves patients' acceptance. It also has an integrated computer using a new algorithm based on the Bernstein-Shramek formula, which allows on-line calculation of Stroke Volume (SV) and Cardiac Output (CO). (C. Jewkes and others: *British Journal of Anaesthesia* 1991; 67:788 794).

The device is used to measure cardiac output (CO), stroke volume (SV), heart rate (HR), and basal impedance (Zo) or thoracic fluid index (TFI). Two "sensing" electrode pairs are placed on the thorax at the level of the mid-axillary line and on the lateral aspect of the neck. The other two pairs of the "current injecting" electrodes are located 5 cm above the cervical, and below the thoracic sensing electrodes. The current injecting electrodes deliver a 2.5 mA, 70 KHz, alternating current.

The comparison of the EBM results, supplied by the BoMED® NCCOM3, with the Thermodilution readings, have shown reasonable correlation coefficients.

However, remarks concerning the BoMED® apparatus, it has been shown in several studies (C. Jewkes); (Francis G. Spinale); (Kou Chu Huang and others, *Critical Care Medicine,* 1990, Vol 18, No. 11), that:

the apparatus overestimates at low and underestimates at high values of cardiac output. In other words, there is no linearity in the measuring characteristics; and the apparatus is critical to the form, type and placement of the electrodes.

U.S. Pat. No. 4,807,638 (B. Shramek and assigned to BoMED®) continues to describe the development of the equipment, based on EBM. A non-invasive continuous mean arterial blood pressure monitor processes the electrical impedance across two segments of body tissue (thorax and legs) to provide a signal for each segment that indicates the increase in blood flow in each segment at the beginning of each cardiac cycle. The cardiac output of the patient is also measured and the cardiac index of the patient is calculated from the cardiac output.

It should be noted, that the monitor's measuring unit comprises a current source having a high frequency constant amplitude electrical current output. The second segment's appearance in the monitor reflects the necessity of obtaining more representative information concerning the human body's hemodynamic parameters. However, the second segment's readings cannot substitute for the integral picture of the human body's hemodynamic parameters. The electrodes, used in the monitor, are arranged on the two segments in the way described in the previous reference. It means that an unpredictable error will appear due to each pair of the excitation and measuring electrodes and due to the distance between these pairs.

The regular segmentary thoracic EBM method and the same disposition of the excitation and measuring electrodes are used in the new BoMED® model 2001 Hemodynamic Management System HDMS. A constant magnitude alternating current having a frequency of 70 KHz and a magnitude of 2.5 mA flows through the thorax. The apparatus does not demonstrate any revolutionary approach to the problem.

Analyzing the systems, which implement Kubicek's and Shramek's method, it should be noted that they are not accurate for the following reasons:

1. Calculation of all the main "volume" hemodynamic parameters (Stroke volume, Cardiac output, etc.) is accomplished by using the derivative of the Impedance (dZ/dt), but not the Impedance itself (Z) or its active component (R), being the direct characteristics of the fluid volume.
2. Non reliable results of calculations are achieved owing to nonlinearity of the impedance and necessity to provide complicated current corrections.
3. Dispersion of the measuring current out of the segment measured in the other parts of the body.
4. Geometry of the particular chest or other segments is not taken into consideration.
5. Errors occurring owing to the initial non-accurate electrodes' dislocation on the thorax, and their displacement caused by respiration.
6. Quite high error of calculations owing to the fact, that ($\delta Z$) is measured relatively to the partial, segmentary (Z) of the body, but not relatively to the total (Z) of the whole body.
7. The necessity of the second channel's signal (ECG) for synchronization of the measurements, in addition to the rheogram signal, results in a plurality of electrical wires needed for the patient's examination.

Moreover, these systems do not obtain and calculate parameters, characterizing the respiratory system.

One of the latest local EBM techniques which have been recently developed is described in U.S. Pat. No. 5,178,154 assigned to Sorba Medical Systems, Inc. There is disclosed an impedance cardiograph and method of operation thereof, utilizing peak aligned ensemble averaging which provides high measurement accuracy.

However, the Sorba system still suffers several drawbacks. Thus, in the first instance, the measurements are provided by a tetrapolar system of electrodes which is complex, inconvenient to the patient and results in artifacts.

Secondly, the main parameter to be measured (Cardiac Stroke Volume) is computed by the Sorba system from a limited area section under a line of the mathematical derivative of the bioimpedance curve of a cardiac cycle. More particularly, this area reflects only the phase of the fast ejection of blood by the heart, and thus cannot reflect all specific processes of blood distribution taking place during a complete cardiocycle (and having an influence on the cardiac parameters).

Thirdly, owing to the fact that the Sorba system provides the thoracic impedance measurements, signals characterizing cardiac activity are much weaker (10%) than carrier signals of respiratory cycles; however, the small cardiac activity signals in Sorba's system are thoroughly sorted out, averaged and processed, while the respiratory oscillations are considered as artifacts and are not analyzed. It is understood, that when using such an approach the respiratory parameters cannot be defined, and the accuracy of calculations of cardiac parameters may be difficult to achieve.

Also known is the so-called Integral EBM of the whole body, enveloping practically the entire blood conducting system. This technique is described by M. Tishcenko (1968), Yakovlev (1973), Holzer (1970) and others. The integral EBM is a priori more informative than the segmentary EBM; however, no appropriate technical realization thereof has been recorded.

The Integral EBM of the whole body was originally suggested by M. Tishcenko (for example, Tishcenko M. I.: *The biophysical and integral basis of integral method for determination of stroke volume of human blood system;* Abstract of Ph.D. dissertation, Moscow, 1971). This method includes applying electrodes not to a segment, but to the whole human body; conveying a low alternating current having a frequency of 30 KHz, passing through the whole body; measuring the whole body's impedance with a rheograph having a measuring bridge; separation of the active component of the impedance by manual tuning, and using it for the subsequent calculations.

The integral EBM method thus described enables the operator to obtain information, concerning the whole cardiovascular system of the body; the main hemodynamic parameters are obtained using different empiric equations derived by M. Tishenko for the integral measurements. Owing to the larger length of the body, embraced by the electrodes, calculation errors can be minimized. The method uses a bipolar electrode system, which is simpler and less prone to error than the tetrapolar Kubicek's system used in the segmentary type EBM method.

However, the system used by M. Tishcenko, needs to be calibrated before every measurement; it also requires tuning in order to exclude the reactive component of the impedance. The other problem is the error, caused by the reactive component, appearing between the electrodes and the skin at the place of their contact. This error is almost impossible to remove by tuning. The accuracy of the calculations completely depends on the manual adjustment, thus rendering the Tishcenko system unreliable.

Research accomplished by the applicant prior to making the present application was intended to satisfy the requirements of modern clinical investigations, such as:

obtaining complete information concerning cardiorespiratory parameters, which can be provided only by means of the integral EBM of the complete human body, such as:

hemodynamic parameters:
Stroke Volume
Systolic Index
Pulse rate
Cardiac output
Heart Index
Reserve Index
Total Resistance Index
Index of Tone Stabilization;

Respiratory parameters:
Rate of respiration
Index of Respiration changes
Index of Respiration intensiveness;
Index of Hemodynamic Security;

and additional important parameters, such as:
Volume of Extracell Fluid of the whole body
Index of Fluid balance of the whole body;

obtaining results of high accuracy and reproducibility when compared with the invasive Thermodilution method; and reducing the error, which may be caused by the type, construction and placement of the electrodes used in the measuring system.

The non-invasive method and system, which were investigated by the applicant, were effected by applying four electrodes to the extremities of a patient's body, introducing an alternating current via the four electrodes through the patient's body; further obtaining the integral impedance curve of the human body from these electrodes; and applying a computerized calculation of the cardiorespiratory parameters of the complete patient's body and parameters concerning the extracell fluids of the patient's body from the integral bioimpedance curve, using empiric formulae applicable to integral bioimpedance measurements.

However, when performing measurements with the above-mentioned four electrodes system, a relatively weak integral bioimpedance signal is still received from the human body.

One reason for this effect is that the measuring current is dissipated over a plurality of the chest arteries of the patient, as well as over the four of the patient's extremities, acting like parallel branches of the electric circuit. Secondly, the measuring current flow which passes through the human's body in the four electrodes system is not mainly directed through the real targets of the measurements, such as the heart and the chest part of the patient's aorta.

These two factors have a negative influence on the reliability of the measurements. Moreover, four electrodes which are to be applied to the human body, still cause a certain amount of inconvenience to the patient and to the operator.

SUMMARY OF THE INVENTION

It is therefore an object of the present invention to provide a non-invasive integral EBM method and system for the determination of the main cardiorespiratory parameters of the human body, being patient-friendly, resulting in a high calculation accuracy to be accomplished by the computerized system, and having a secured electrodes' contact to the patient's body when taking the required measurements.

According to a first aspect of the invention, there is provided a non-invasive method for determining of the main cardiorespiratory parameters of the human body, comprising the steps of:

applying electrodes to the patient's body in a manner enabling to obtain integral bioimpedance measurements of the total body of a patient;

introducing a high stability amplitude alternating current through said electrodes into said body;

obtaining an integral impedance curve of said body from the electrodes;

providing simultaneous automatic separation of an active component from said integral impedance; and applying a computerized calculation of the cardiorespiratory parameters of said body from the active component of said integral bioimpedance, using empiric formulae applicable to integral bioimpedance measurements;

the calculation being accomplished based on the average data obtained during a respiration cycle.

In accordance with a preferred embodiment, four electrodes are connected in two pairs to the extremities of a patient's body; each pair being used both for current injection and voltage measuring.

By comparison with the situation where only two electrodes are applied, it has been found that connecting only two electrodes enables:

the current dispersion to be reduced throughout the patient's body and extremities;

the main current flow to be applied to the heart and the chest part of the patient's aorta, these being the major target of the investigation;

the measured integral bioimpedance of the patient's body to be increased, thus increasing the accuracy of further calculations of the needed parameters;

the other two extremities of the patient to be freed for other possible treatments or patient's simultaneous activities;

the influence of random movement or tremor of the patient's legs and/or hands to be reduced.

It should be noted that if any pathological changes are found in the extremities of the patient, or if some specific extremities are in the process of other kinds of treatments at the same moment, alternative less preferable combinations of the electrodes' positions can be used. More particularly, the two electrodes may be either connected to the distal parts of the right arm and the left leg, or to the right arm and the right leg, or to the left arm and the left leg.

According to a second aspect of the invention, there is provided a non-invasive medical device for determining at least one cardiorespiratory parameter of the human body, said device comprising:

at least two electrodes, electrical total body integral bioimpedance measuring unit coupled to the electrodes and including a high stability amplitude alternative current source and an electronic circuit for automatic derivation of an active component of said integral bioimpedance; and a computer coupled to the electrical integral bioimpedance measuring unit and to a display means for calculating and displaying said at least one cardiorespiratory parameter from the active component of the integral bioimpedance.

In a preferred embodiment, two electrodes are applied to the patient's body according to a bipolar system, so as to be used both for current ejection and voltage measurement, the two electrodes being connected to the electrical bioimpedance measuring unit via a single channel.

BRIEF DESCRIPTION OF THE DRAWINGS

In order to understand the invention and to see how the same may be carried out in practice, some preferred embodiments will now be described, by way of non-limiting example only, with reference to the accompanying drawings, in which:

FIG. 1A is a block diagram showing functionally a measuring system according to the invention using four electrodes;

FIG. 1B is a schematic circuit diagram representing the system shown in FIG. 1A;

FIG. 1C is a block diagram showing functionally a measuring system according to the invention using two electrodes;

FIG. 1D is a schematic circuit diagram representing the system shown in FIG. 1C;

FIGS. 1E, 1F and 1G depict modifications of the system shown in FIG. 1C;

DETAILED DESCRIPTION OF PREFERRED EMBODIMENTS

Figure 2A:
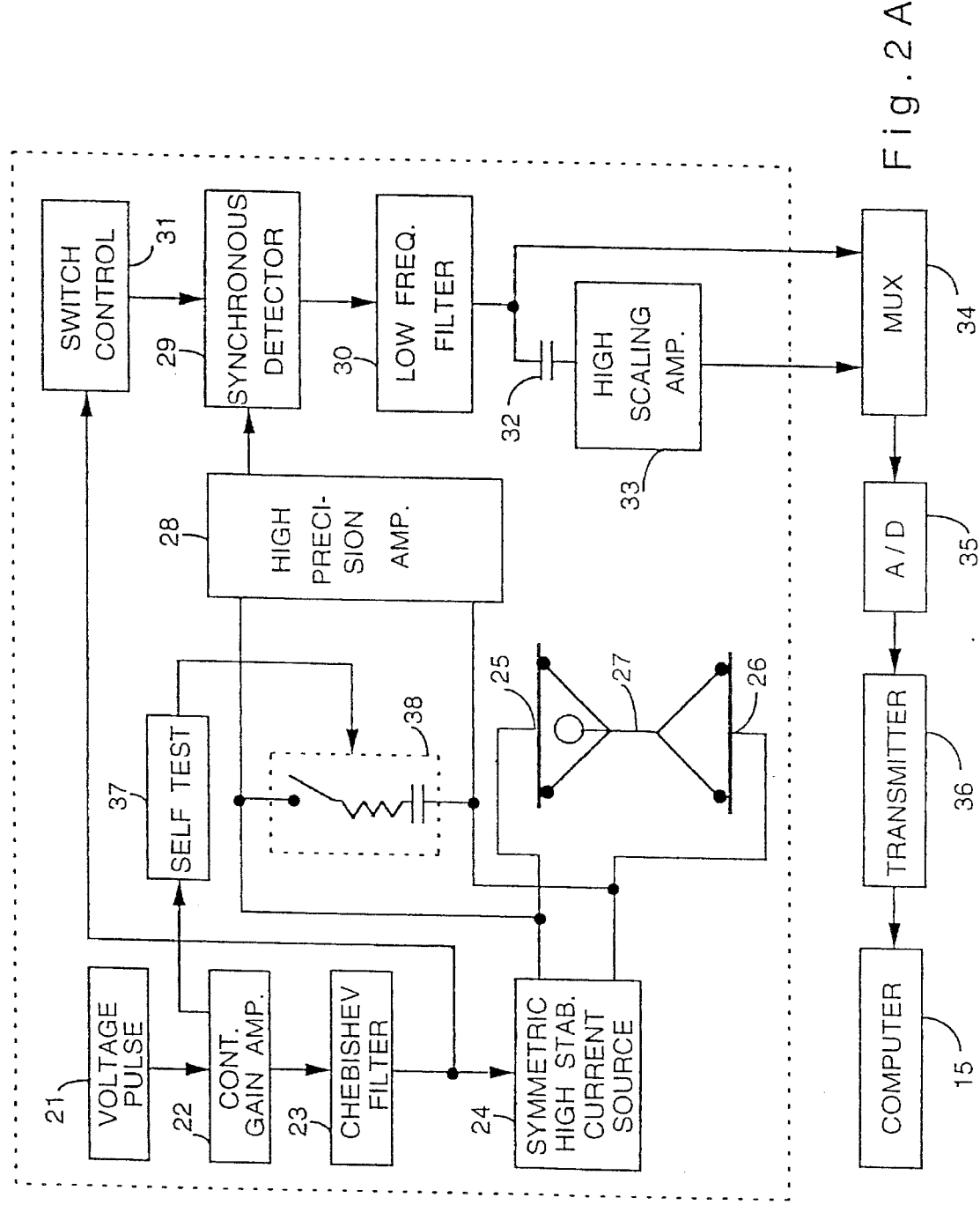
FIG. 2A is a block diagram showing schematically an electrical integral bioimpedance measuring system according to the invention.

FIGS. 1A and 1B show respectively a block-diagram of a non-invasive four-electrode system for automatic express determination of the main cardiorespiratory parameters of a patient 10 and an equivalent electrical circuit diagram of the patient 10.

Four electrodes 11, connected in two pairs, are applied to the distal parts of the arms and legs of the patient 10. An electrical integral bioimpedance measuring unit 12 delivers a high stability amplitude alternating current through a single channel 13, via the electrodes 11 to the patient 10. The integral impedance curve of the patient 10 is obtained from the same electrodes 11 and is transferred through the same single channel 13 to the measuring unit 12, which converts the integral impedance curve. The converted working signal is then transferred through a second single channel 14 to a computer 15, where cardiorespiratory parameters of the whole body and parameters concerning extracell fluids of the whole body are calculated using empiric formulae.

During a Monitoring Mode, personal data characteristic of the patient 10 which is entered into the computer 15 via a keyboard (not shown). Typically, the personal data includes height, weight, age, sex, results of a blood test, identification index, etc. An output signal 14 from the electrical integral bioimpedance measuring unit 12 is fed to the computer 15 and are stored in an internal table therein. Preliminary processing of the raw data is performed so as to derive a plethysmographic and rheographic curve, on the basis of which the respiratory cycle and heart beat complex indices (marks) are determined (the beginning of the anacrotic slope, the length of heart complexes' cycle, their maximum amplitude, etc.). The area section under the initial impedance curve reflecting the phases of the fast and slow ejection of the blood during a cardiocycle is used for computing the main parameters. Based on this data and the patient's personal data, the parameters are determined using empiric formulae, newly developed by E. Frinerman, one of the inventors of this invention.

The basic hemodynamic parameter Stroke Volume (SV) is calculated according to the following equation:

$$SV = \frac{Hct_{corr.}}{K(shape*sex*age)} * \delta r \frac{H^2_{corr.}}{R} * \frac{\alpha+\beta}{\beta} * kel * Kw * IB \quad (1)$$

where:

$Hct_{corr.}$—a corrected Haemotacrytis, being 145+ 0.35(Hct−40);

Hct—Haemotacrytis, obtained from the blood analysis of the patient;

K(shape*sex*age)—a complex coefficient of the individual patient's body, being:

men younger than 20 years old =

527.3 − (3.1 * (Actual Age −20));

women younger than 18 years old =

587.6 − (2.9 * (Actual Age −18));

men older than 40 years old =

527.3 + (3.1 * (Actual Age −40));

women older than 50 years old =

587.6 + (2.9 * (Actual Age −50));

δr/R—the ratio characterizing the measured active bio-impedance component's change;

$H_{corr}$—the corrected height of the patient, given by:

$$H_{corr} = (H_{real} + 2) \text{ if } \frac{\text{body length}}{\text{legs length}} = 0.66 \pm 0.04 \qquad (2)$$

or $$H_{corr} = (H_{real} - 2) \text{ if } \frac{\text{body length}}{\text{legs length}} = 0.54 \pm 0.04$$

α+β—duration of a cardiac cycle, being a sum of its anacrotic and catacrotic parts;

β—duration of the catacrotic part of a cardiac cycle;

Kel —coefficient of electrolytic ions in the patient's blood, calculated based on the blood analysis and being given by:

a) for the patients exposed to a hemodialysis $$Kel = \frac{(Na^+ + K^+ + Mg^+ + Ca^+)(mmol/l)}{142 + 13(mmol/l)} \qquad (3)$$

b) for other patients $$Kel = \frac{(Na^+)(mmol/l)}{142(mmol/l)} \qquad (4)$$

$K_w$  the weight coefficient, being $\frac{\text{Actual weight}}{\text{Ideal weight*}}$

*(according to the International Tables of ideal weights)

IB   Index Balance, given by the following ratio:

$$IB = \frac{\text{The measured volume of extracellular fluids}}{\text{The proper volume of extracellular fluids}} \qquad (5)$$

The above described novel equation demonstrates that individual differences in a bioimpedance of a specific human body can be considered by correcting the formula according to the particular features of the patient's body.

The computer 15 is programmed to calculate a plurality of parameters based on the above definition of the Stroke Volume equation. For example, the following parameters can be computed:

Index of Respiration Changes (IRC) is calculated according to the following formulae, reflecting the Stroke Volume changes relatively to respiration:

$$IRC = \frac{Y_{max} * \frac{\alpha+\beta}{\beta} \text{ of the same cardiocycle}}{Y_{min} * \frac{\alpha+\beta}{\beta} \text{ of the same cardiocycle}} \qquad (6)$$

where:

$Y_{max}$ is the maximal amplitude of the anacrotic part of a cardiocycle, defined during one respiration cycle; and $Y_{min}$ is the minimal amplitude of the anacrotic part of a cardiocycle, defined during the same respiration cycle;

$$\frac{\alpha+\beta}{\beta}$$

see the explanation of (SV) calculation, equation (1).

The Extracellular fluid Volume of the whole body (Vecf) (by M. Tishcenko equations):

$$V_{ecf} = K * H^2 * R^{-1} * 10^{-3} \qquad (7)$$

where:

K is a coefficient, being 95 for male and 115 for female;

R is the patient's body resistance; and

H is the patient's height.

FIGS. 1C and 1D show respectively a block-diagram of a non-invasive two-electrode system for automatic express determination of the main cardiorespiratory parameters of a patient 10 and an equivalent electrical circuit diagram of the patient 10.

A first electrode 11a is connected to the distal part of the left arm, and a second electrode 11b to the distal part of the patient's right leg. All the other elements of the system remain the same as the system described above and depicted in FIG. 1A.

It should be noted, that owing to the difference between the equivalent electric diagrams of the patient 10 used in the system shown in FIGS. 1B and 1D, the integral bioimpedance of the patient as measured by the system of FIG. 1C will be higher than that measured by the system according to FIG. 1A, as explained above. This enables a stronger initial signal to be obtained, thus improving the accuracy of the further electric transformations and calculations to be accomplished by the system.

Moreover, the current flow is mainly directed through the heart and the chest part of the patient's aorta, being the actual target for the measurements; and the current is less dissipated throughout the extremities and chest arteries. These two factors improve the reliability of the measurements. Moreover, the described two-electrode system is more patient-friendly than the four-electrode system and also enables an operator to effect simultaneously some additional needed measurements or treatments on the patient's second arm or leg.

Some other possible variants of the electrodes connection are showed in FIGS. 1E to 1G. In each case, either two or four electrodes may be connected to the patient. In case of the former, the arrangement reduces to the bipolar system described above with reference to FIGS. 1C and 1D of the drawings. If the electrodes which are shown dotted are also connected, then the arrangement describes a tetrapolar scheme in which two of the electrodes are active for injecting the current, whilst two of the electrodes are passive for detecting the resultant signal.

Calculation of parameters to be accomplished by this modified system needs specific corrections in comparison with hitherto-proposed calculations for the four-electrode system. These corrections may be effected by means of adjusting of the empiric coefficients as defined above.

FIG. 2A is a block-diagram of the electrical integral bioimpedance measuring unit depicted as 12 in FIGS. 1A and 1C. It should first be noted, that the human body behaves, from an electrical point of view, as an RC impedance. The operation of the unit 12 described below clarifies the method suggested in the present application.

The electrical integral bioimpedance measuring unit 12 comprises a voltage pulse generator 21, producing 30 KHz rectangular pulses. These pulses are directed to a controllable gain amplifier 22 an outlet of which is connected to a Chebishev filter 23 for converting the signal to a sinusoidal form. The outlet of the filter 23 is connected to an inlet of a symmetric high stability amplitude alternating current source 24. The high stability amplitude current maintained at the outlets of the current source 24, is applied through two pairs of electrodes 25, 26 to the human body 27.

The voltage signal, proportional to the human body impedance Z (constituting an integral bioimpedance) is generated within the patient's body and transferred from the electrodes 25, 26 to a high precision amplifier 28, whose outlet is fed to a first input of a synchronous detector 29. The synchronous detector 29 has two functions: first, it rectifies the obtained integral bioimpedance; and secondly, it provides simultaneous derivation of the active component of the integral bioimpedance voltage vector. This component is directly proportional to the resistive component of the load (resistance of the blood system as stated by Tishcenko).

The second function is provided with the aid of a switch controlling scheme 31, connected at an inlet thereof to an outlet of the filter 23, and at an outlet thereof to a second input of the synchronous detector 29.

The linear behavior of the synchronous detector 29 simplifies the calibration process and reduces it to a one time, initial adjustment (instead of a per cycle calibration).

A low frequency filter 30 being, for example, a low pass Bessel filter, is connected to an outlet of the synchronous detector 29. The low-pass filter 30 cuts off high frequency components, for example above 32 KHz, and delivers a working signal. The working signal, being the active bioimpedance component, is then divided by a capacitor 32 into a direct component and an alternating component. The alternating component is amplified by a high scaling amplifier 33 and is fed together with the direct component to respective inlets of a multiplexer 34. An output of the multiplexer 34 is connected to an analog-to-digital (A/D) converter 35, which is connected to the computer 15 (FIGS. 1A and 1C) through a transmitter 36.

Also provided is a self-testing block for testing the unit before starting the measurements comprising a control unit 37 connected to the second outlet of the controllable gain amplifier 22 and a simulating impedance circuit 38 connected across the patient's body 27.

Figure 2B:
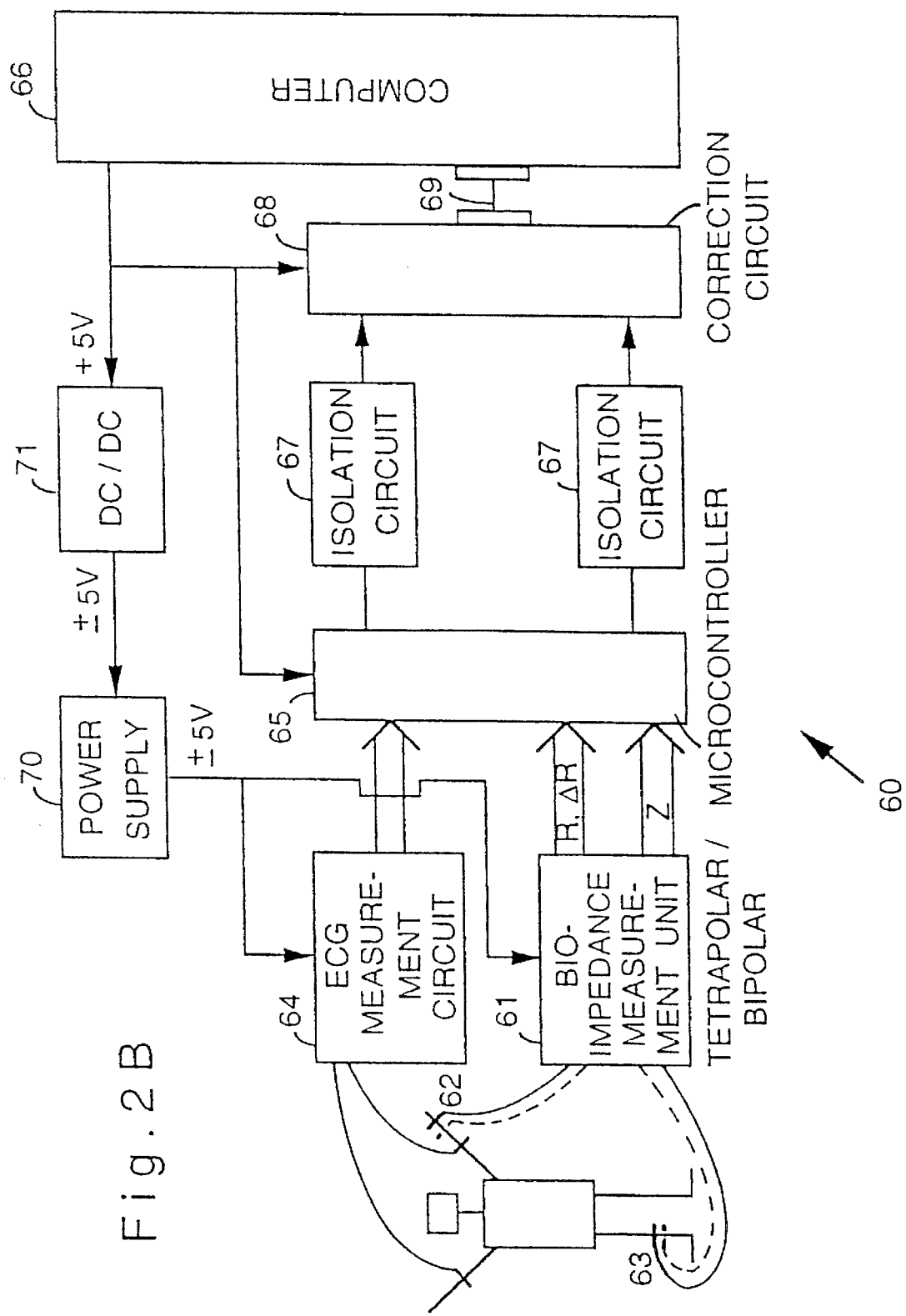
FIG. 2B is a block diagram showing a modification of the instrument shown in FIG. 2A.

FIG. 2B is a block-diagram of a modification 60 of the unit of the instrument described above with reference to FIG. 2A of the drawings. The Bioimpedance Measuring Unit which is depicted in FIG. 2A within a dashed line, is now shown as 61. It should be noted, however, that two electrodes 62, 63 are now applied to two of the patient's extremities, and are now shown outside the Bioimpedance Measuring Unit 61 (as opposed to the four electrodes shown in FIG. 2A inside the dashed contour). Two additional ECG electrodes are applied to the arms of the patient and connected to an ECG measurement circuit 64.

A micro-controller 65 (such as model 80196KC manufactured by Intel®) combining the functions of the A/D converter and a microprocessor, is provided for processing in real time a curve obtained from the ECG circuit 64, together with the curve obtained from the Bioimpedance Measuring Unit 61 and being a composition of a direct "R" and an alternating "δR" components of an active bioimpedance component. Additionally, the micro-controller 65 receives the initial complete bioimpedance curve from the Bioimpedance Measuring Unit 61 (more particularly from the output of the High Precision Amplifier 28 shown in FIG. 2A). When processing both the initial bioimpedance curve and the curve of the active bioimpedance component, the micro-controller 65 and a computer 66 (such as a note-book computer) continuously calculate a capacitance of the electric circuit of the human body. The value of the capacitance of the human body can be calculated by the formula:

$$Z = R - \frac{j}{\omega C} \qquad (8)$$

and continuously checked.

An excess of the capacitance over a predetermined threshold, or oscillation of the capacitance indicates degradation of the contacts between the electrodes and the patient's skin. In such case, an appropriate alarm is activated under control of the computer 66. The outputs of the micro-controller 65 are connected to the computer 66 via isolation circuits 67 (such as opto-isolators MOC 8080, Motorola®) providing electrical protection of the patient from a random voltage, via a correction circuit 68 (such as the driver RS232C) and an appropriate RS232C cable 69. The correction circuit 68 and the micro-controller 65 are supplied with electrical voltage of +5 V from the computer 66. The voltage +5 V is converted to ± 5 V by a DC/DC converter 71, which is further connected to a power supply unit 70. The DC/DC converter 71 also performs a function of an isolation circuit. The power supply unit 70 provides the blocks of the instrument 60 with electrical voltage +5 V.

Figure 3A:
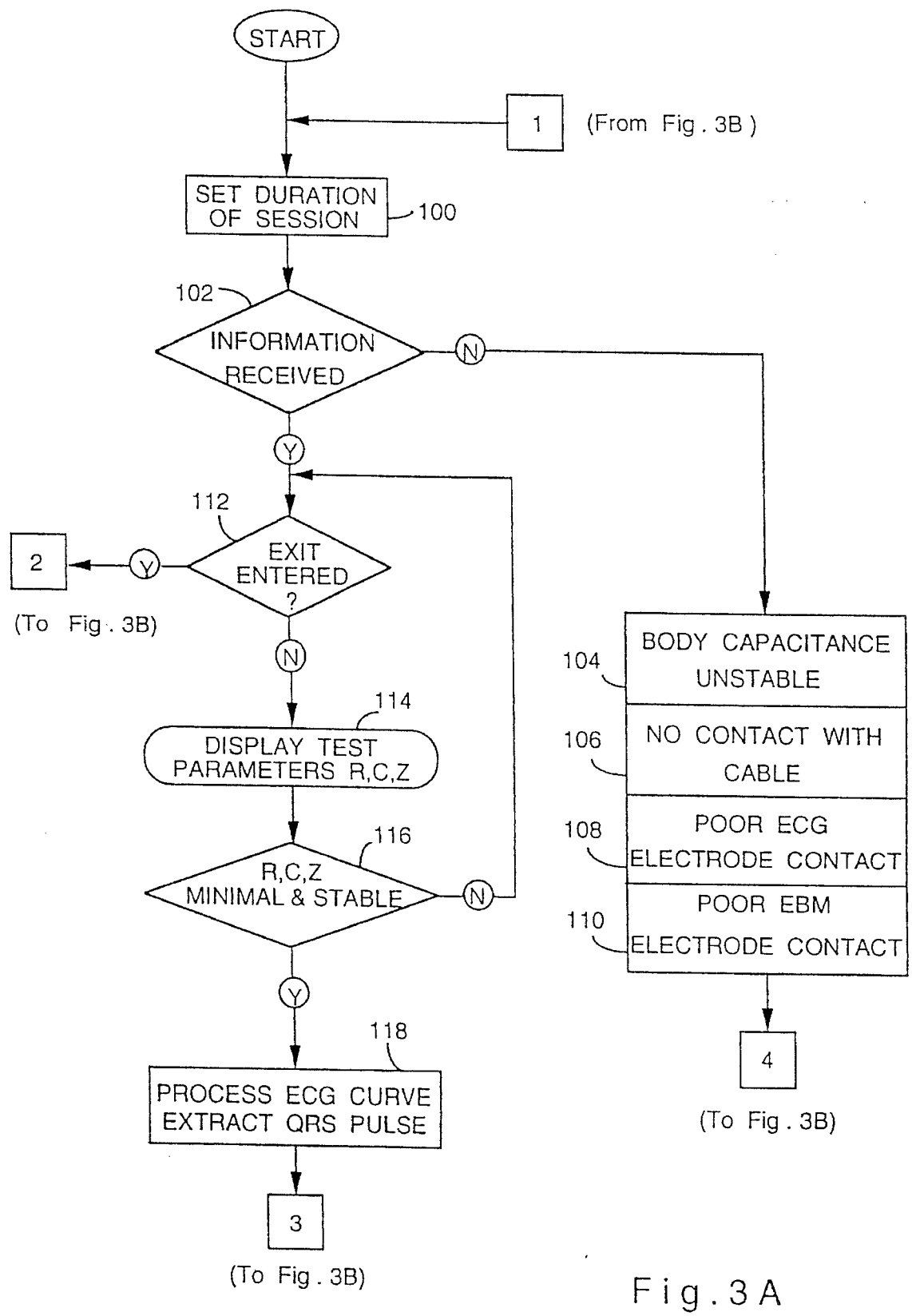
FIGS. 3A and 3B are a flowchart showing the principal steps in a method for using the measuring system according to the invention.
Figure 3B:
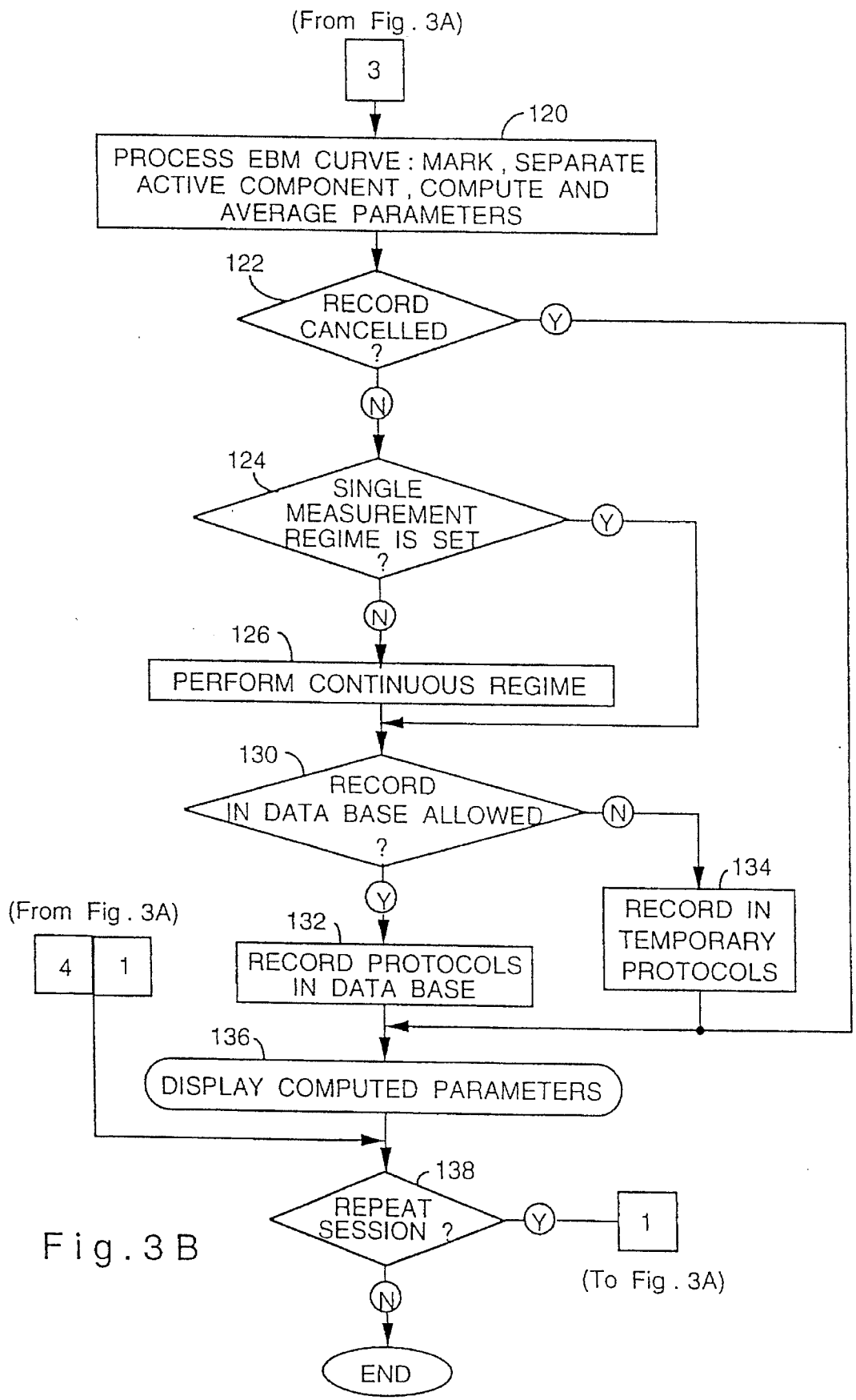

FIGS. 3A and 3B shows a flow diagram of an algorithm in accordance with which the system functions.

At step 100 the system is switched on, and the duration of the monitoring session is chosen. The duration of the monitoring session can be defined as a duration of an initial bioimpedance curve section intended for an averaged calculation of the necessary parameters, and can be chosen in the range of about 10 to 30 sec.

At step 102 a check is performed in order to determine whether the information from the Bioimpedance Measurement Unit 61 is obtained on the display. If not, the reason should be detected and indicated by at least one of the following test blocks:

Block 104—The impedance between electrodes and the skin is not stable;

Block 106—There is no contact in the cable RS232C;

Block 108—The ECG electrodes contact is poor;

Block 110—A poor contact of the bioimpedance measuring electrodes.

After overcoming the reason for the malfunction, the cycle should be started again (returning to step 102). If no exit command were keyed by an operator (block 112), the digital test readings of R (active impedance), C (capacitance), and Z (complete impedance) will be displayed in real time on the display (step 114).

When these parameters are stabilized (step 116), the next procedure is started wherein the QRS pulse is derived from the ECG curve (step 118) for marking the bioimpedance curve.

Step 120 represents the processes of marking of the bioimpedance curve by the marks obtained at step 118, further processing of the rheographic information and computing the main cardiorespiratory parameters being based on the average data obtained during a respiration cycle.

If a record of the computed parameters is not aborted at step 122, the parameters should be stored in the computer. The parameters in the system can be computed either in a regime of a single measurement (step 124), or in a continuous regime (step 126).

The computed parameters may be stored in the computer in one of the following two ways: the values of the parameters can be either entered into a data base of the patient in the computer (step 132), or the parameters can be written down as a temporary protocol in the computer (step 134). At step 130 it is decided whether or not the data base should be used for the record of the computed parameters.

When the single monitoring session is finished, a plurality of the computed parameters are indicated on the display (step 136). At step 138 there is defined whether or not to repeat the measurements. The order to repeat the measurements can be entered either manually by the operator, or automatically, if the continuous regime were chosen. If such an order is received, another monitoring session will be started, and additional readings of the parameters will be recorded. If the measurements are not to be repeated, the process will be stopped at step 140.

Figure 4:
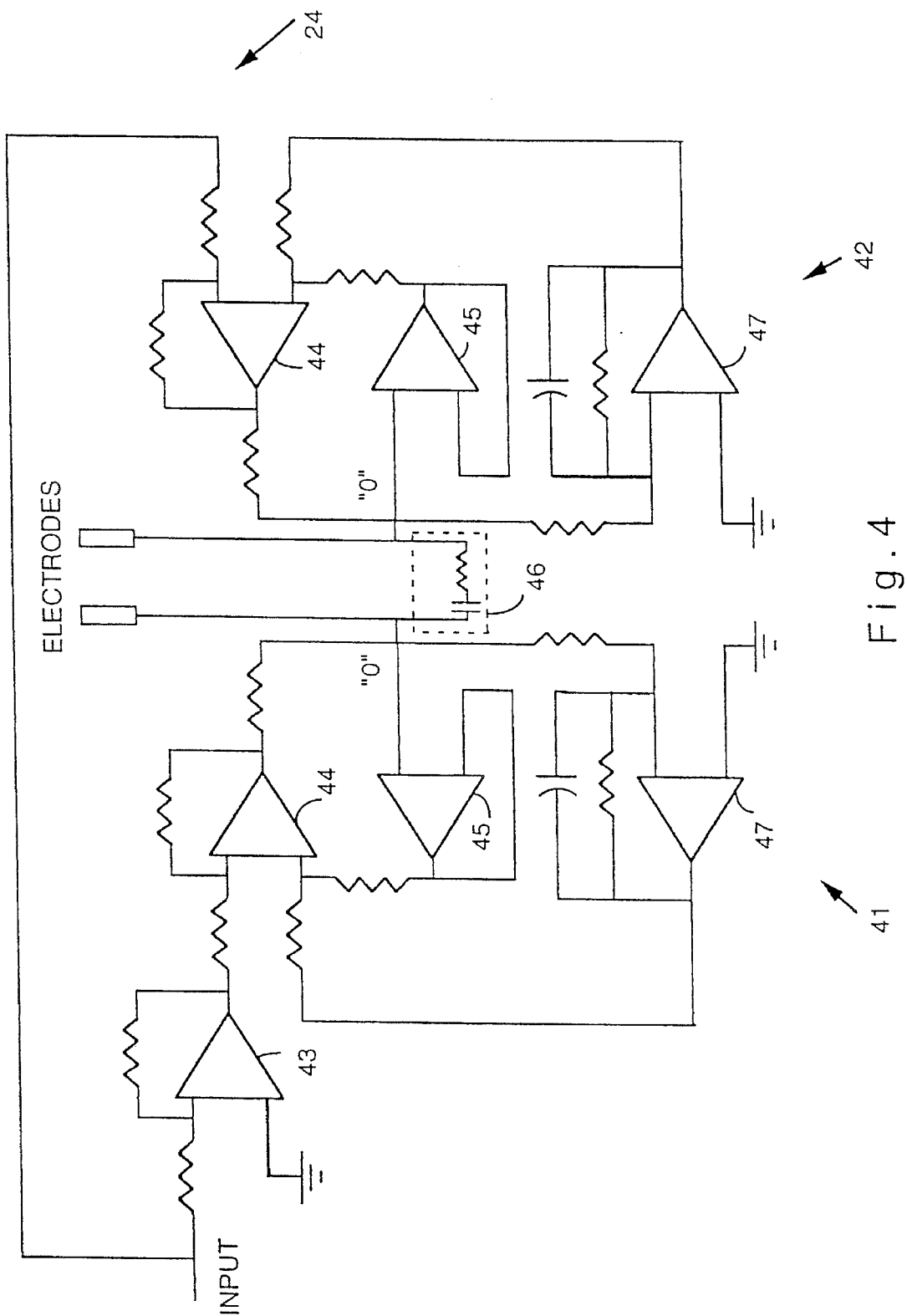
FIG. 4 is an electrical circuit diagram of the high stability amplitude alternative current source shown in FIG. 2A.

FIG. 4 shows an electrical scheme of the source of the high stability amplitude alternative current across an RC load. The current source 24 has a symmetric structure in order to minimize errors and noise appearing in the output signal. The second feature is its high stability ($10^{-5}$ to $10^{-7}$). The variations in the resistance, due to heartbeat and respiration cycles, are in the range of $10^{-3}$ of the total value. In order to make the measurements of these variations reliable, the stability of this circuit has to be at least two orders of magnitude greater.

The high stability amplitude alternative current source 24 comprises first and second symmetric current sources 41 and 42, in order to minimize errors appearing in the output signal. The two symmetric current sources 41, 42 are connected to the voltage pulse generator 21 through the amplifier 22 and filter 23 (see FIG. 2A). The input point is shown as "input" in FIG. 4. The first current source 41 is connected to the "input" through an inverter 43, and the second symmetric current source 42 is connected to the "input" directly.

The first current source 41 stabilizes the positive half-wave alternating voltage input, and the second current source 42 stabilizes the negative half-wave alternating voltage input. Each of the symmetric current sources 41, 42 comprises three high precision operational amplifiers in conjunction with associated circuitry. The first operational amplifier 44, having a high output resistance, is fed with the alternating signal from the "input" point at the inverting inlet. A positive feedback is formed on the amplifier 44 by a second high precision, high speed operational amplifier 45. The first and second operational amplifiers 44, 45 stabilize the alternating current, passing over the RC load 46. The outlet of the first operational amplifier 44 and the non-inverting inlet of the second operational amplifier 45 form a zero point "0".

Owing to the high output resistance of any current source, stray currents or an asymmetric input voltage may deter the current source from the operating. In order to prevent this, the third operational amplifier 47, in conjunction with its appropriate circuitry, is connected at its inverting inlet to the zero point "0", and at its outlet to the non-inverting inlet of the first operational amplifier 44. The operational amplifier 47 provides a zero voltage DC level at the zero point "0", thus maintaining the current source in correct working condition. The load 46, being a human body, is connected to two symmetric zero points of the two symmetric current sources 41, 42.

Figure 5:
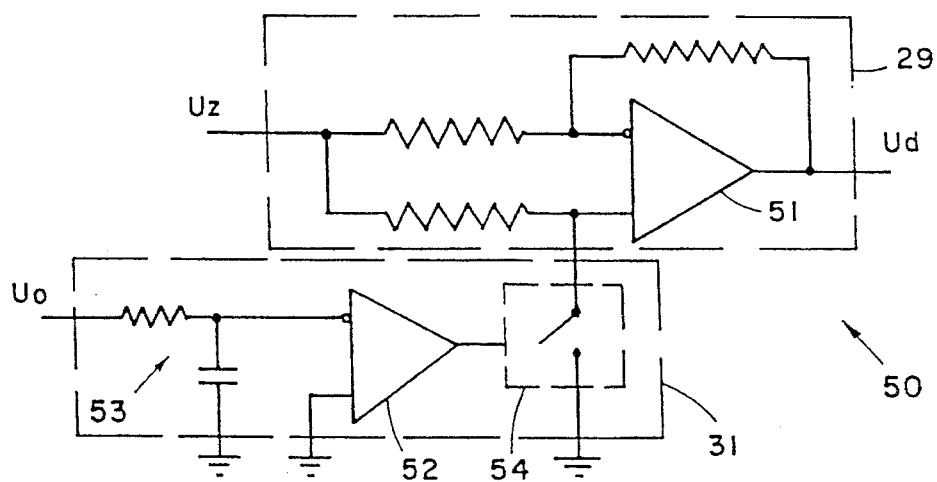
FIG. 5 is an electrical circuit diagram for achieving automatic separation of the active component from the integral bioimpedance.
Figure 6:
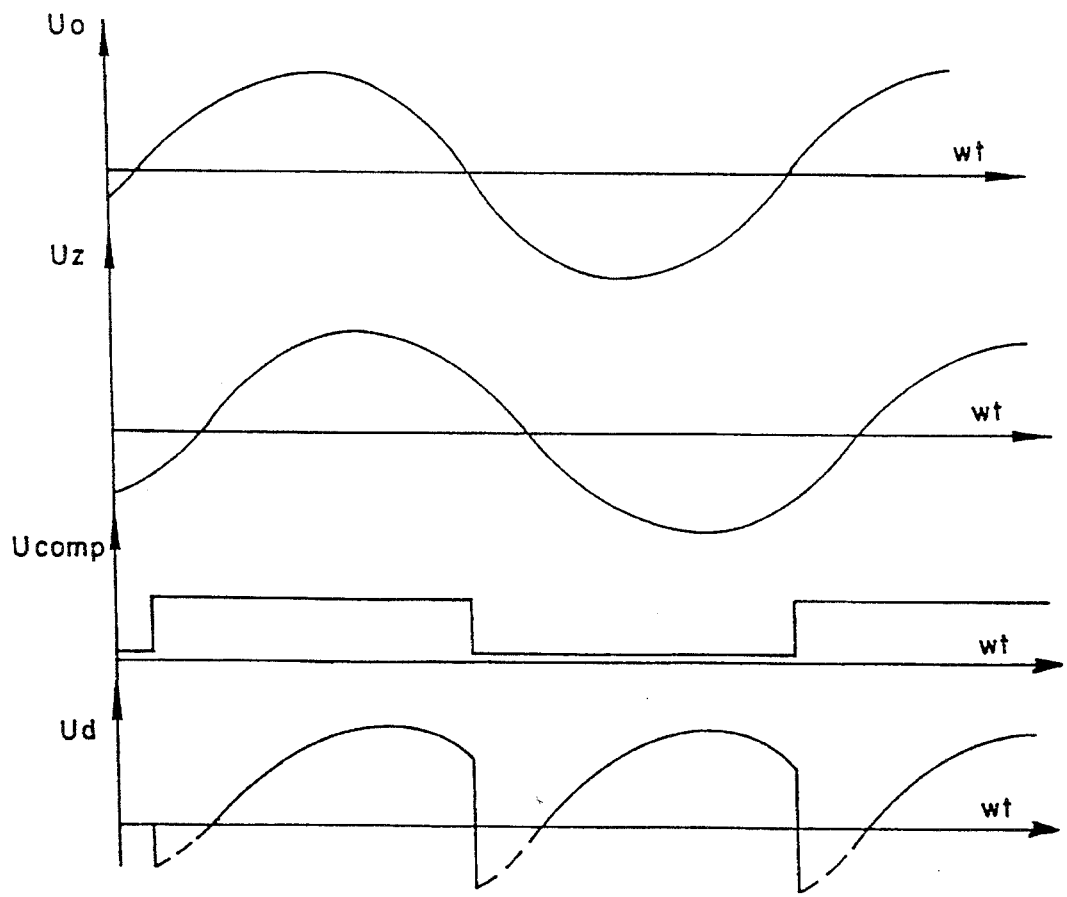
FIG. 6 is a timing diagram relating to operation of the circuit shown in FIG. 5.

FIGS. 5 and 6 show respectively the electronic circuit 50 for automatic derivation of the active component from the integral bioimpedance, and a time diagram describing the circuit's operation. The circuit is constituted by the synchronous-detector 29, associated with the switch controlling scheme 31 in FIG. 2A.

The circuit 50 comprises first and second operational amplifiers 51 and 52, respectively. The first operational amplifier 51 is connected at its inlets to the high precision amplifier 28 (see FIG. 2A). The second operational amplifier 52, functioning as a comparator, is connected at its inverting inlet to the outlet of the filter 23 (FIG. 2A) through an RC timing circuit 53. An outlet of the second operational amplifier 52 is connected to the non-inverting inlet of the first operational amplifier 51 through an electronic switch 54. The RC timing circuit 53 is intended to remove a delay in the triggering of the comparator 52 and the switch 54.

The electronic circuit 50 operates as follows. An alternating voltage $U_z$ from the outlets of the high precision amplifier 28 is applied to the both inlets of the first operational amplifier 51. The voltage $U_z$ is proportional to the voltage appearing across load constituted by the human body and represents its bioimpedance.

An alternating voltage $U_o$ from the outlet of the filter 23 is applied to one inlet of the comparator 52 through the RC timing circuit 53. Owing to the fact, that the voltage $U_o$ activates the high stability amplitude alternative current source 24, this voltage is proportional to the current $I_o$, passing through the human body load.

It can be seen on the timing diagram, that the $U_z$ curve is delayed relative to the $U_o$ curve; the delay being predetermined by the reactive component of the human body load. If $U_o$ becomes positive, the comparator 52 will immediately turn off the switch 54 (see the $U_{comp}$ curve), and a voltage will appear on the outlet of the amplifier 51 whose magnitude is given by:

$$U_d = K * U_z \qquad (9)$$

where:

K is an amplifying coefficient.

If $U_o$ becomes negative, the comparator immediately operates the switch 54, and the amplifier 51 inverts the input voltage, whereupon the output voltage will be:

$$U_d = -K * U_z \qquad (10)$$

Hence, the scheme described accomplishes detection of the input voltage $U_z$. The $U_d$ curve has positive sections, which can characterize the active component of the $U_z$ voltage curve by their duration and amplitude.

The positive $U_d$ voltage is filtered by the low frequency filter 30 (FIG. 2A). At the outlet of the filter 30 an alternating voltage $U_f$ is created, equal to the average value of the $U_d$ voltage. Voltage $U_f$ can be described by the following equations:

$$U_f = \frac{(2I_m * K * Z)}{T} * \int_0^{\frac{T}{2}} \sin(\omega t + \phi) dt \qquad (11)$$

$$= (I_o * Z * K) \frac{1}{T} \cos\phi$$

where:

$I_m$ is the amplitude of the current passing through the load;

K is the amplifying coefficient=$U_d/U_z$;

$\omega$ is the angular frequency;

$\phi$ is the delay angle between the current and voltage curves;

$$\tan\phi = \frac{1}{\omega CR} \quad (12)$$

Z the impedance of the load being given by:

$$Z = \frac{R}{\cos\phi} \quad (13)$$

$$= \sqrt{R^2 + \left(\frac{1}{\omega C}\right)^2}$$

T is the period of the sinusoidal signal.
Using all these data it may be shown that:

$$U_f = \frac{R}{T}(I_m * K) \quad (14)$$

Hence, the voltage $U_f$ appearing on the outlet of the filter 30 is proportional to the active component R of the bioimpedance of the human body.

It has been shown that the method according to the invention comprises applying the electrodes according to either a bipolar or tetrapolar system. In either case, a preliminary connection of four electrodes may be effected to the respective distal parts of the human extremities, whereafter the integral impedance is preliminarily measured between each pair of electrodes placed on each arm and leg. Determination of the main cardiorespiratory parameters of the human body is made in accordance with which pair of electrodes is characterized by the lowest integral impedance.

In accordance with one embodiment, the method according to the invention further includes a computerized calculation of parameters concerning extracellular fluids of the patient's body, the calculations being based on measurements accomplished at two different current frequencies.

It should further be noted that the method according to the invention may also be employed for revealing the pathological extremities, where arterial blood circulation defects occur or another pathological defect takes place.

Moreover, if both of the upper extremities are under treatment or have associated therewith pathological defects (thrombophlebitis, tremor, oedema), or if the patient needs to be monitored for a long period of time, or has to have his arms free for other types of treatment or for required physical exercises, other arrangements of the electrodes' connection can be effected, especially for measuring of cardio-parameters.

In the preferred embodiment a plurality of such parameters are calculated by said method, including hemodynamic parameters such as Stroke Volume, Systolic Index, Pulse Rate, Cardiac Output, Heart Index, Reserve Index, Total Resistance Index, Index of Tone Stabilization; and respiratory parameters such as Rate of Respiration, Index of Respiration changes, Index of Respiration Intensiveness, Index of Hemodynamic Security; and additional parameters, such as Index of Respiratory Duration and Index of Tidal Respiratory Volume.

In yet a further embodiment, a plurality of parameters characterizing extracellular fluids of the human body are calculated, such as Volume of Extracellular Fluids of the whole patient's body and Index of Fluid Balance of the whole body.

While the present invention has been described with the reference to the attached drawings, it should be appreciated, that other embodiments of the described system and its elements can be suggested and should be considered as part of the invention.

We claim:

1. A non-invasive method for determining of the main cardiorespiratory parameters of a human body, comprising the steps of:

attaching electrodes to the body in a manner so as to enable the measuring of integral bioimpedance measurements of the total body of a patient;

transmitting a high stability amplitude alternating current through said electrodes and into said body;

obtaining an integral impedance curve of said body from the connected electrodes upon transmission of the high stability amplitude alternating current;

transmitting the integral impedance curve to a measuring device;

converting the impedance curve to a working signal;

transmitting the working signal to a computer;

simultaneously and automatically separating an active component from said integral impedance;

calculating cardiorespiratory parameters; and applying the computerized calculation of the cardiorespiratory parameters of said body from the active component of said integral bioimpedance, using empiric formulae applicable, to integral bioimpedance measurements;

the computerized calculation being based on the bioimpedance measurements measured during a respiration cycle.

2. The method according to claim 1, further including the step of:

calculating, in said computer, parameters relating to extracellular fluids of the patient's body; said parameters being based on bioimpedance measurements measured at two different current frequencies.

3. The method according to claim 1, further comprising the steps of:

attaching four electrodes to the extremities of a patient's body; said four electrodes being combined into two pairs, each pair being used both for current injection and voltage measuring.

4. The method according to claim 1, further comprising the step of:

attaching two electrodes at two distal parts of the patient's extremities respectively, so as to include the patient's body as part of an electrical circuit formed between said electrodes.

5. The method according to claim 4, further comprising the steps of attaching one of the two electrodes to a distal part of a left arm, and attaching the second electrode at a distal part of a right leg of the patient.

6. The method according to claim 1, further including the steps of:

preliminarily attaching four of said electrodes to respective distal parts of extremities of the patient;

measuring an integral impedance between each pair of said electrodes placed on each arm and leg; and selecting, for determination of the main cardiorespiratory parameters of the human body, the pair of electrodes characterized by a lowest integral impedance.

7. The method according to claim 1, further comprising the step of attaching the electrodes in a bipolar manner.

8. The method according to claim 1, further comprising the step of attaching the electrodes in a tetrapolar manner.

9. The method according to claim 1, further including the step of continuously examining each electrode's contact by continuously setting a local capacitance between the electrode and the patient's skin during said measurement, and activating an alarm whenever said capacitance exceeds a minimal threshold.

10. The method according to claim 1 for calculating a plurality of said parameters further including the steps of:

obtaining hemodynamic parameters from the patient including Stroke Volume, Systolic Index, Pulse rate, Cardiac output, Heart Index, Reserve Index, Total Resistance Index, Index of Tone Stabilization;

obtaining respiratory parameters from the patient including Rate of respiration, Index of Respiration changes, Index of Respiration intensiveness, Index of Hemodynamic Security; and obtaining additional parameters from the patient including Index of Respiratory Duration and Index of Tidal Respiratory Volume.

11. The method according to claim 10, further comprising the step of calculating a plurality of parameters characterizing extracellular fluids of the human body including Volume of Extracellular Fluids of the whole patient's body and Index of Fluid Balance of the whole body based upon the parameters obtained.

12. The method according to claim 1, further comprising the step of calculating a basic hemodynamic parameter Stroke Volume according to the following equation:

$$SV = \frac{Hct_{corr.}}{K(shape*sex*age)} * \delta r \frac{H^2_{corr.}}{R} * \frac{\alpha+\beta}{\beta} * kel * Kw * IB$$

where:

$Hct_{corr.}$—a corrected Haemotacrytis, being $145 + 0.35(Hct-40)$;

Hct—Haemotacrytis, obtained from the blood analysis of the patient;

K(shape*sex*age)—a complex coefficient of the individual patient's body, being:

men younger than 20 years old =

$527.3 - (3.1 * (\text{Actual Age} -20))$;

men older than 40 years old =

$527.3 + (3.1 * (\text{Actual Age} -40))$;

women younger than 18 years old =

$587.6 - (2.9 * (\text{Actual Age} -18))$;

women older than 50 years old =

$587.6 + (2.9 * (\text{Actual Age} -50))$;

$\delta r/R$—the ratio characterizing the measured active bioimpedance component's change;

$H_{corr.}$—the corrected height of the patient, given by:

$H_{corr} = (H_{real} + 2)$ if $\frac{\text{body length}}{\text{legs length}} = 0.66 \pm 0.04$ or $H_{corr} = (H_{real} - 2)$ if $\frac{\text{body length}}{\text{legs length}} = 0.54 \pm 0.04$ $\alpha+\beta$—duration of a cardiac cycle, being a sum of its anacrotic and catacrotic parts;

$\beta$—duration of the catacrotic part of a cardiac cycle;

Kel—coefficient of electrolytic ions in the patient's blood, calculated based on the blood analysis and being given by:

a) for the patients exposed to a hemodialysis $$Kel = \frac{(Na^+ + K^+ + Mg^+ + Ca^+)(mmol/l)}{142 + 13(mmol/l)}$$

b) for other patients $$Kel = \frac{(Na^+)(mmol/l)}{142(mmol/l)}$$

$K_w$ the weight coefficient, being $\frac{\text{Actual weight}}{\text{Ideal weight*}}$

*(according to the International Tables of ideal weights)

IB Index Balance, given by the following ratio:

$$IB = \frac{\text{The measured volume of extracellular fluids}}{\text{The proper volume of extracellular fluids}}.$$

13. A non-invasive medical device for determining at least one cardiorespiratory parameter of a human body, the device comprising:

at least two electrodes for attachment to the human body, an electrical total body integral bioimpedance measuring device coupled to the at least two electrodes and including a high stability amplitude alternative current source and electronic means for automatically deriving an active component of said integral bioimpedance wherein the measuring device transmits a high stability amplitude alternative current through said at least two electrodes;

a computer coupled to the electrical integral bioimpedance measuring device for receiving a signal transmitted from the measuring device and calculating said at least one cardiorespiratory parameter from the active component of the integral bioimpedance based upon the received signal; and display means connected to the computer for displaying said at least one cardiorespiratory parameter from the active component of the integral bioimpedance.

14. The device according to claim 13, comprising two electrodes, wherein:

said two electrodes are connected to the patient's body in a bipolar manner, so as to be used both for current injection and voltage measurement; and a single channel, the two electrodes being connected to the electrical bioimpedance measuring device via the single channel.

15. The device according to claim 13, comprising four electrodes, wherein:

said four electrodes are connected, in pairs, to two sections of the patient's body in a tetrapolar manner, so that a first pair of the electrodes are used for current injection, and a second pair of the electrodes are used for voltage measurement; and two channels, the four electrodes being connected to said electrical bioimpedance measuring unit via the two channels.

16. The device according to claim 13, wherein the current source transmits a high stability amplitude alternating current from the measuring device through the at least two electrodes and through the patient's body when connected to the at least two electrodes, and wherein the patient's body acts as a resistive capacitance (RC) impedance.

17. The device according to claim 16, wherein the current source has a stability factor of between $10^{-5}$ to $10^{-7}$, and based upon the stability factor variations in bioimpedance in a complete range of $10^{-3}$ are able to be measured by the measuring device.

18. The device according to claim 16, wherein said current source delivers a current of 1 to 2 mA, at a frequency of 32 to 100 KHz through the at least two electrodes and to the patient's body.

19. The device according to claim 13, wherein the electrical integral bioimpedance measuring device comprises:

a voltage pulse generator, a first filter;

a detector, having an output, for detecting the integral bioimpedance signal obtained;

a transmitter;

a controllable gain amplifier having a first terminal coupled to the voltage pulse generator and having a second terminal coupled to the first filter, a high stability amplitude alternative current source coupled to the first filter and having a pair of outlets connected to the at least two electrodes connected across the patient's body, a high precision amplifier, connected across said at least two electrodes for receiving a signal therefrom and having an outlet connected to the detector, and for providing simultaneous separation of its active component from its reactive component, a low-pass filter, coupled to the output of the detector, and having an output for issuing a working signal, a capacitor coupled to the output of the low-pass filter for dividing the working signal into a direct component and an alternating component, a high scaling amplifier coupled to the capacitor for amplifying the alternating component, a multiplexer having a pair of inlets respectively coupled to respective outputs of the low-pass filter and the high scaling amplifier, for alternately connecting either the direct or the alternating components to an input of said multiplexer wherein the outputs of the low-pass filter and high scaling amplifier act as outputs of the measuring device, and an analog-to-digital (A/D) converter having an input connected to the output of the multiplexer and having an output connected to said computer via the transmitter.

20. The device according to claim 19, wherein the detector is provided with a switch control connected between the output of the first filter and the input of the high stability amplitude alternative current source.

21. The device according to claim 20, wherein the detector comprises:

an electronic switch;

an RC timing circuit;

a first operational amplifier having a pair of inputs connected to the high precision amplifier and a second operational amplifier connected at an inverting input thereof to the outlet of the first filter through the RC timing circuit, and at its outlet to the non-inverting input of said first operational amplifier through the electronic switch.

22. The device according to claim 19, wherein:

the electrical integral bioimpedance measuring device is provided with a self testing block for testing the device before obtaining the measurements;

the self testing block comprising:

a control device connected to the second outlet of the controllable gain amplifier, and a means for simulating impedance connected across the patient's body.

23. The device according to claim 19, wherein the analog-to-digital converter, the multiplexer and the transmitter are constituted by a micro-controller, the micro-controller having a plurality of input ports and at least one output port.

24. The device according to claim 23, further comprising:

an ECG measuring device having at least two inputs and an output; and first and second ECG electrodes connected to respective ones of the at least two inputs of the ECG measuring device; and wherein:

the inputs of the high precision amplifier are connected to the at least two electrodes, the outputs of the electrical integral bioimpedance measuring device are connected to respective input ports of the micro-controller, the output of the high precision amplifier is connected to a respective input port of the micro-controller, the output of the ECG measuring device is connected to a respective input port of the micro-controller, and the at least one output port of the micro-controller is connected to the computer via isolation circuits and a correction circuit.

25. The device according to claim 19, wherein the high stability amplitude alternative current source comprises:

an inverter;

two symmetric current sources connected to the voltage pulse generator via the controllable gain amplifier and the first filter, one of said symmetric current sources being connected to the first filter through an inverter, and the second symmetric current source being connected to the first filter directly for receiving an alternating voltage from the first filter;

the first of the symmetric current sources stabilizing a positive half-wave of the alternating voltage, and the second of the symmetric current sources stabilizing a negative half-wave alternating voltage received from the first filter;

and wherein each of the symmetric current sources comprises:

first, second and third high precision operational amplifiers, a first of the high precision operational amplifiers including an output, an inverting input and a non-inverting input, and having a high output resistance and being provided with an alternating signal from the first filter at the inverting input, and being further provided with a positive feedback formed by the second high precision, high speed operational amplifier, the second operational amplifier including an output, an inverting input and a non-inverting input; said first and second operational amplifiers stabilizing the alternating current passing through the load;

the output of the first operational amplifier and the non-inverting input of the second operational amplifier forming a zero point; the third operational amplifier, including an output an inverting input and a non-inverting input, is connected at its inverting input to the zero point, and at its output to the non-inverting input of said first operational amplifier in order to provide a zero voltage DC level at said zero point; and said load, being constituted by a human body, is connected to the symmetric zero point of each of said two symmetric current sources through the at least two electrodes.

* * * * *